United States Patent [19]

Schickaneder et al.

[11] Patent Number: 5,663,381

[45] Date of Patent: Sep. 2, 1997

[54] PROCESS FOR PREPARING FORM 1 RANITIDINE HYDROCHLORIDE

[75] Inventors: Helmut Schickaneder, Eckental; Aggelos Nikolopoulos, Bayreuth, both of Germany

[73] Assignee: Hexal Pharmaceuticals, Inc., Mobile, Ala.

[21] Appl. No.: 426,930

[22] Filed: Apr. 21, 1995

[51] Int. Cl.$^6$ ................................................. C07D 307/52
[52] U.S. Cl. ............................................................ 549/492
[58] Field of Search .............................................. 549/492

[56] References Cited

U.S. PATENT DOCUMENTS

| | | | |
|---|---|---|---|
| 4,128,658 | 12/1978 | Price et al. | 424/285 |
| 4,521,431 | 6/1985 | Crookes | 514/471 |
| 4,672,133 | 6/1987 | Crookes | 549/495 |
| 5,338,871 | 8/1994 | Ngooi et al. | 549/492 |

*Primary Examiner*—Amelia Owens
*Attorney, Agent, or Firm*—Cohen, Pontani, Lieberman, Pavane

[57] ABSTRACT

A process for preparing pure N-[2-[[[5-[dimethylamino)-methyl-2-furanyl]methyl]thio]ethyl]-N'-methyl-2-nitro-1,1-ethyldiamine hydrochloride, designated Form 1 ranitidine hydrochloride, from ranitidine in methylene chloride with the addition of hydrochloric acid. The Form 1 ranitidine hydrochloride thus obtained is stable and therefore useful for producing commercial-scale quantities of Form 1 ranitidine hydrochloride.

30 Claims, 1 Drawing Sheet

PROCESS FOR PREPARING FORM 1 RANITIDINE HYDROCHLORIDE

FIELD OF THE INVENTION

The present invention is concerned with hydrochloride salt of the $H_2$-antagonist N-[2-[[[5-[(dimethylamino)-methyl-2-furanyl]methyl]thio]ethyl]-N'-methyl-2-nitro-1,1-ethyldiamine, also known as ranitine. More specifically, the present invention is concerned with a novel process for the production of Form 1 rantidine hydrochloride.

BACKGROUND OF THE INVENTION

U.S. Pat. No. 4,128,558 granted on Dec. 5, 1978 to Price et al. describes various aminoalkyl furan derivatives including ranitidine. Example 32 of U.S. Pat. No. 4,128,658 in particular describes the preparation of Form 1 ranitidine hydrochloride by dissolving rantidine in industrial methylated spirit (a solvent made up largely of ethanol) containing hydrogen chloride gas, and crystallizing with the addition of ethyl acetate. This procedure is unsatisfactory because of the instability of Form 1 rantidine hydrochloride in the described solvent crystallization system which contains ethyl acetate and ethanol. In particular, the process is inadequate for large scale production.

U.S. Pat. Nos. 4,521,431 and 4,672,133 granted to Crookes on Jun. 4, 1985 and Jun. 9, 1987, respectively, describe a crystalline form of rantidine hydrochloride which is designated as Form 2 and which purportedly has more favorable filtration and drying characteristics than the Form 1 ranitidine hydrochloride obtained from the process using hydrogen chloride gas in industrial methylated spirit and ethyl acetate, as described in Example 32 of U.S. Pat. No. 4,128,558. The Form 2 ranitidine hydrochloride of Crookes may be prepared by treating a solution of ranitidine in a hydroxylic solvent, e.g., a lower alkanol, with hydrochloric acid followed by crystallization at elevated temperatures by adding further quantities of solvent. Alternatively, Form 2 ranitidine hydrochloride may be prepared from previously isolated Form 1 or Form 2 ranitidine hydrochloride by dissolving the salt, e.g., by warming in an organic solvent such as methanol or ethanol, followed by cooling to cause crystallization of the Form 2 salt, optionally accompanied by the addition of an anti-solvent or by the addition of Form 2 seeds to induce crystallization.

The differences between Form 2 as described in U.S. Pat. Nos. 4,521,431 and 4,672,133 and Form 1 which is the product of Example 32 of U.S. Pat. No. 4,128,658 are characterized by infra-red spectra and x-ray powder diffraction patterns.

U.S. Pat. No. 5,338,871 to Ngooi et al. is directed to the preparation of pure Form 1 ranitidine hydrochloride by forming a solution of ranitidine hydrochloride in a solvent mixture comprising at least one lower aliphatic alcohol, preferably ethanol, and an aromatic hydrocarbon, preferably toluene, and initiating crystallization by seeding with crystals of pure Form 1 ranitidine hydrochloride.

Ranitidine hydrochloride Forms 1 and 2 both have histamine $H_2$-blocking activity. However, because of the progressing difficulties experienced with Form 1, e.g., its sensitivity to moisture and the inability to produce it in commercial quantities, Form 2 has been produced exclusively and used as the active ingredient in the treatment of conditions where there is hypersecretion of gastric acid, such as gastric and peptic ulceration, and in the treatment of allergic conditions where histamine is a known mediator. Form 2 is also used in the treatment of allergic and inflammatory conditions.

So that Form 1 may also be used to treat these conditions, there is a need for a process that will consistently produce pure and stable Form 1 ranitidine hydrochloride without any coproduction of, or conversion to, Form 2.

OBJECTS AND SUMMARY OF THE INVENTION

It is therefore an object of the present invention to provide a process for preparing pure Form 1 ranitidine hydrochloride which will remain stable over an extended period of time.

It is also an object of the present invention to provide a process for preparing seeding material of pure Form 1 ranitidine hydrochloride for use in large scale production of pure Form 1 ranitidine hydrochloride.

The present invention is thus directed to a process for the preparation of pure Form 1 ranitidine hydrochloride comprising dissolving ranitidine in a solvent, mixing the solution thus obtained with hydrochloric acid to form a reaction mixture, and crystallizing Form 1 ranitidine hydrochloride from the reaction mixture. The ranitidine which may be employed herein is disclosed in U.S. Pat. No. 4,128,658 mentioned above. More particularly, the process of the present invention comprises the steps of dissolving ranitidine in methylene chloride, adding hydrochloric acid, with or without cooling, to the solution thus obtained, mixing the solution to form a reaction mixture, heating the reaction mixture under reflux and while heating, stripping off water under azeotropic conditions to thereby produce Form 1 ranitidine hydrochloride crystals. The Form 1 ranitidine hydrochloride crystals that are so formed are then filtered out, washed with ethanol and dried. These crystals can be used as seeds to induce further crystallization that will result in large scale production quantities of pure Form 1 ranitidine hydrochloride, (See Example 6 below), without any co-production of, or conversion to, Form 2 ranitidine hydrochloride.

The present invention is also directed to pure Form 1 ranitidine hydrochloride produced by the processes herein described and characterized by its infra-red spectrum.

DETAILED DESCRIPTION OF THE PRESENTLY PREFERRED EMBODIMENTS

Figure 1:
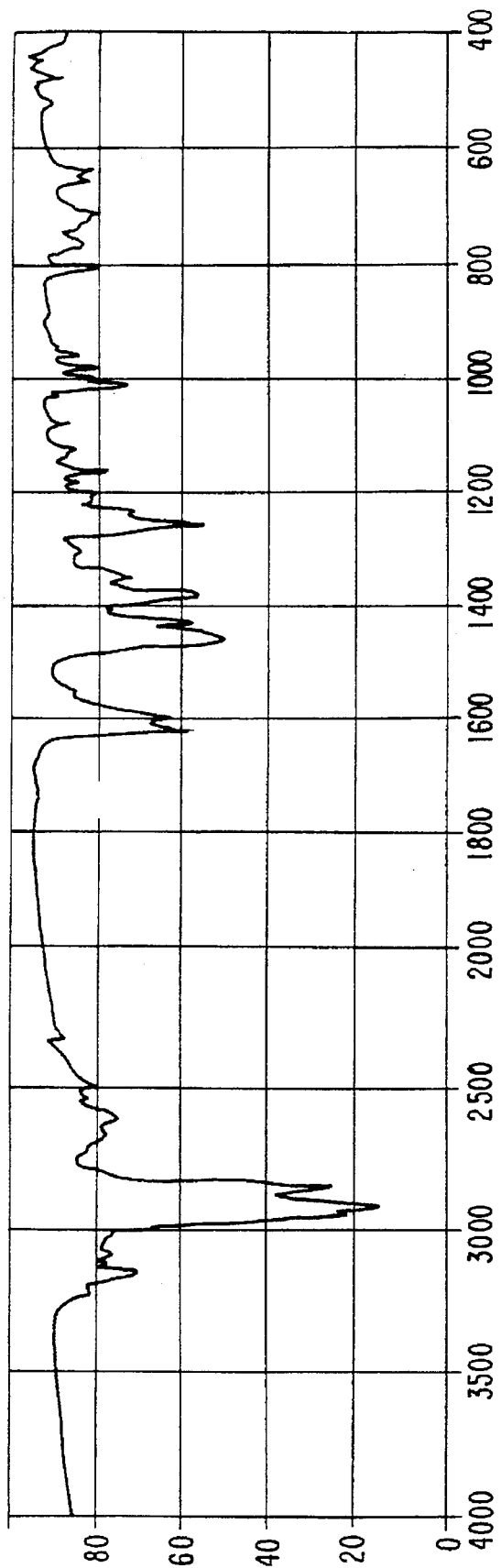
FIG. 1 is an infra-red spectrum of Form 1 ranitidine hydrochloride of the present invention in a KBr pellet where the ordinate is the transmittance in % and the abscissa is the wavenumber in $cm^{-1}$.

The present invention provides a process for the preparation of pure Form 1 ranitidine hydrochloride. More particularly, the present invention provides a process for preparing pure Form 1 ranitidine hydrochloride which, among other uses, may be used as seeding material to produce large scale quantities of pure Form 1 ranitidine hydrochloride in a second process.

The seeding material of pure Form 1 ranitidine hydrochloride may be prepared by dissolving ranitidine in a solvent, preferably methylene chloride, at room temperature (20° to 25° C.), wherein the ratio of ranitidine to methylene chloride is from about 1:1 to 1:5, preferably 1:4, and treating the solution thus obtained with aqueous concentrated hydrochloric acid (e. g., 35 to 38% w/w). The hydrochloric acid and ranitidine may be mixed without cooling to form a reaction mixture. Preferably, however, the hydrochloric acid and ranitidine are mixed with cooling at −5° C. to 10° C. The reaction mixture is then heated under reflux and during heating, water is stripped off under azeotropic conditions. Preferably, the reaction mixture is heated under reflux for at least 4 hours, more preferably for approximately 6.5 hours. Alternatively, the reaction may be carried out under mild reaction conditions, such as, for example from 0° to 10° C. up to 20° to 25° C. for approximately 6.5 hours. The Form 1 ranitidine hydrochloride crystals that are formed are then filtered off from the crystallization medium, washed with ethanol and dried.

Alternatively, the seeding material of pure Form 1 ranitidine hydrochloride may be prepared by first introducing a solvent, preferably methylene chloride, into preferably a first oxygen-free reactor (1) at 20°–25° C. Ranitidine is then added to the solvent and the solution thus obtained is agitated for about 10 minutes and then cooled to about 0° to −5° C.

Into preferably a second oxygen-free reactor (2), a solvent, preferably methylene chloride, is introduced and cooled to about −5° C. After charging reactor (2) with hydrogen chloride gas at −5° C., the cold ranitidine solution of reactor (1) is slowly added to reactor (2) to form a reaction mixture, the temperature of the mixture being maintained at about −5° to 0° C. and the pH at about 6 to 6.8. (It is important to keep the pH acidic so as to avoid co-production of Form 2 ranitidine hydrochloride.) After stirring the reaction mixture for several hours, crystallization of pure Form 1 ranitidine hydrochloride occurs. The Form 1 ranitidine hydrochloride crystals that are formed are then filtered out by centrifugation, for example, and dried under vacuum at a maximum of 40° C. for about 2 to 3 hours.

Among the uses for these Form 1 ranitidine hydrochloride crystals is as a seeding material in the large scale production process to be described below.

When production quantities of pure Form 1 ranitidine hydrochloride are desired, a preferred method is to first introduce into preferably an oxygen-free reactor pure ethanol rather than solvents such as, for example, toluene and ethylacetate. At 15° to 20° C., ranitidine is added to the ethanol and stirred for approximately 15 minutes to dissolve the ranitidine. The ratio of ranitidine to ethanol is from about 1:2 to 1:4, preferably about 1:3.6. Aqueous hydrochloric acid (35%) is then added to the solution thus obtained until a pH of 6± about 0.2 at about 30° C. is reached. While maintaining this acidic pH and a temperature of from about 30° to 35° C., the seeding material of pure Form 1 ranitidine hydrochloride (as produced by the alternate process described above) is added to the solution in a concentration of about 3% to 20% by weight. Preferably, the concentration of the seeding material in the solution is approximately between about 4% to 7% by weight. Within about one hour, crystallization of pure Form 1 ranitidine hydrochloride occurs. The Form 1 ranitidine hydrochloride crystals that are formed are then filtered out by centrifugation, for example, and dried under vacuum at a maximum of 40° C. for about 2 to 3 hours.

Stability test results of the compound. Form 1 ranitidine hydrochloride and tablets containing Form 1 ranitidine hydrochloride confirm the retention of the Form 1 polymorph for at least six months of storage at 40° C./75% relative humidity.

The present invention also provides for pure Form 1 ranitidine hydrochloride produced by the processes herein described and characterized by its infra-red spectrum as shown in FIG. 1.

Form 1 ranitidine hydrochloride may be formulated for administration in any convenient way and the invention includes within its scope pharmaceutical compositions comprising Form 1 ranitidine hydrochloride adapted for use in human or veterinary medicine. Such compositions may be presented for use in a conventional manner with the aid of a pharmaceutically acceptable carrier or excipient and may also contain, if required, other active ingredients, e.g., $H_1$-antagonists. Thus the hydrochloride salt according to the invention may be formulated for oral, buccal, topical, parenteral, or rectal administration. Oral administration is preferred, particularly in the form of tablets and capsules.

For oral administration, the pharmaceutical composition may take the form of, for example, tablets, capsules, powders, solutions, syrups or suspensions prepared by conventional means with acceptable excipients. For buccal administration the compositions may take the form of tablets or lozenges formulated in a conventional manner.

Form 1 ranitidine hydrochloride may be formulated for parenteral administration by bolus injection or continuous infusion. Formulations for injection may be presented in unit dosage form in ampules or in multi-dose containers, with an added preservative. The compositions may take such forms as suspensions, solutions or emulsions in oily or aqueous vehicles, and may contain formulatory agents such as suspending, stabilizing and/or dispensing agents. Alternatively, the active ingredient may be in powder form for reconstitution with a suitable vehicle, e.g., sterile pyrogen-free water, before use.

Form 1 ranitidine hydrochloride may also be formulated in rectal compositions such as suppositories or retention enemas, e.g., containing conventional suppository bases such as cocoa butter or other glycerides.

For topical application, Form 1 ranitidine hydrochloride may be formulated as ointments, creams, gels, lotions, powders or sprays in a conventional manner.

For internal administration, dosage must be adjusted to the individual needs of each patient. In general, the manufacturer's specifications for any drag or drag combination are useful guides to administration. *The Physician's Desk Reference* or other suitable publication can also be consulted to ascertain appropriate drag levels. Nonetheless, the typical adult dosage can range from 100 mg daily to as much as 6 g daily depending upon the severity of the symptoms being treated. For example, for the treatment of active duodenal ulcer, the usual adult dosage is 150 mg twice daily. For the treatment of pathological hypersecretory conditions, the usual adult dosage is 150 mg twice daily but may be administered more frequently if necessary. For the treatment of erosive esophagitis, the usual adult dosage is 150 mg four times daily.

The present invention is more particularly described and explained by the following examples. It should be understood, however, that the preferred embodiments and examples described are for illustrative purposes only and are not to be construed as limiting the scope of the present invention which is properly delineated only in the appended claims.

EXAMPLE 1

50 g (0.16 mole) of ranitidine was dissolved in 250 mls of methylene chloride at room temperature. Without cooling, 14.9 mls (0.167 mole) of concentrated aqueous HCl solution were added. The temperature of the emulsion rose by up to 6° C. and the pH of the oily phase ranged from 2.5 to 3.

The reaction mixture was then heated under reflux for 6.5 hours. During heating of the mixture 10.5 mls of water were stripped off under azeotropic conditions. The hydrochloride of ranitidine Form 1 crystallized. After filtration, washing with absolute ethanol, and drying, 53.4 g of Form 1 ranitidine hydrochloride were obtained.

EXAMPLE 2

50 g (0.16 mole) of ranitidine was dissolved in 250 mls of methylene chloride at room temperature. Without cooling, 15.6 mls (0.175 mole) of concentrated aqueous HCl solution were added. The temperature of the emulsion rose by up to 6° C. The pH of the oily phase ranged from 2 to 2.5. Refer to Example 1 for the remaining. steps of the procedure.

52.6 g of Form 1 ranitidine hydrochloride were obtained.

EXAMPLE 3

100 g (0.32 mole) of ranitidine was dissolved in 500 mls of methylene chloride at room temperature. Without cooling, 34 mls (0.382 mole) of concentrated aqueous HCl solution were added. The temperature of the emulsion rose by up to 12° C. The pH of the oily phase was 2. Refer to Example 1 for the remaining steps of the procedure.

111.2 g of Form 1 ranitidine hydrochloride were obtained.

EXAMPLE 4

18.86 g (0.32 mole) of HCl gas were introduced into 1000 mls of methylene chloride at room temperature. To this solution 130 g of ranitidine dissolved in 390 mls methylene chloride were added at 20° C. without cooling. The pH of the oily phase was 2. After seeding with a known Form 1 ranitidine HCl the oily phase crystallized. Refer to Example 1 for the remaining steps of the procedure.

103.5 g of Form 1 ranitidine hydrochloride were obtained.

EXAMPLE 5

120 liters of methylene chloride were introduced into a 600 liter oxygen-free reactor (1) at room temperature. 40 kgs of ranitidine were added to this solvent. After agitating for 10 minutes the solution was cooled to 0°—5° C.

In a second oxygen-free reactor (2), 200 liters of methylene chloride were introduced and cooled to −5 ° C.

4.5 kgs of HCl-gas were charged at −5° C. While keeping the temperature at −5° C. to 0° C., a sufficient amount of the cold ranitidine solution of reactor (1) was added slowly until the pH ranged from about 6 to 6.8. After stirring the reaction mixture for several hours, Form 1 ranitidine hydrochloride crystallized.

Form 1 ranitidine hydrochloride was dried under vacuum at a maximum of 40° C. for 2–3 hours.

42 kgs of Form 1 ranitidine hydrochloride were obtained.

EXAMPLE 6

1080 liters of ethanol were introduced into an oxygen-free reactor.

At 15°–20° C., 300 kgs of ranitidine were added to the solvent. This solution was stirred for 15 minutes to dissolve the ranitidine.

Via a dispenser 85 liters of a 35% aqueous hydrochloric acid solution were added until a pH value of 6±0.2 at 30° C. was reached. To this solution 17 kgs of the seeding crystals of Form 1 ranitidine hydrochloride (produced in Example 5) were added at 30°–35° C. The value was 6±0.2.

After 1 hour pure Form 1 ranitidine hydrochloride was crystallized. After centrifugation, ranitidine hydrochloride was dried under vacuum at 40° C. 305 kgs of Form 1 ranitidine hydrochloride were obtained.

It should be understood that the preferred embodiments and examples described are for illustrative purposes only and are not to be construed as limiting the scope of the present invention which is properly delineated only in the appended claims.

What is claimed is:

1. A process for preparing pure Form 1 ranitidine hydrochloride, which comprises: dissolving rantidine in a solvent comprising methylene chloride; mixing the solution thus obtained with hydrochloric acid to form a reaction mixture; and crystallizing Form 1 ranitidine hydrochloride from the reaction mixture.

2. The process according to claim 1, further including the steps of heating the reaction mixture under reflux and while heating, stripping off water under azeotropic conditions.

3. The process according to claim 2, wherein the reaction mixture is heated under reflux for at least 4 hours.

4. The process according to claim 3, wherein the reaction mixture is heated under reflux for approximately 6.5 hours.

5. The process according to claim 1, wherein the ranitidine and hydrochloric acid are mixed with cooling at −5° to 10° C.

6. The process according to claim 1, wherein the ranitidine is dissolved in said solvent at room temperature.

7. The process according to claim 6, wherein the ratio of ranitidine to methylene chloride is from about 1:1 to 1:5.

8. The process according to claim 7, wherein the ratio of ranitidine to methylene chloride is about 1:4.

9. A process for preparing Form 1 ranitidine hydrochloride, which comprises: dissolving ranitidine in ethanol at 15° to 20° C., the ratio of ranitidine to ethanol being from about 1:2 to 1:4; mixing the solution thus obtained with hydrochloric acid to form a reaction mixture having a pH of 6± about 0.2; and while maintaining this acidic pH and a temperature of from about 30° to 35° C., adding seeding material of Form 1 ranitidine hydrochloride to the reaction mixture in a concentration of 3% to 20% by weight, whereby crystallization of Form 1 ranitidine hydrochloride occurs.

10. The process according to claim 9, wherein the ratio of ranitidine to ethanol is about 1:3.6.

11. The process according to claim 9, wherein the seeding material is added in a concentration of 4% to 7% by weight.

12. Form 1 ranitidine hydrochloride prepared by dissolving ranitidine in methylene chloride, the ratio of ranitidine to methylene chloride being from about 1:1 to 1:5, mixing the solution thus obtained with hydrochloric acid to form a reaction mixture, heating the reaction mixture under reflux, and while heating, stripping off water under azeotropic conditions to form crystals of Form 1 ranitidine hydrochloride without any coproduction of, or conversion to, Form 2 ranitidine hydrochloride.

13. The Form 1 ranitidine hydrochloride of claim 12, wherein the ratio of ranitidine to methylene chloride is about 1:4.

14. Form 1 ranitidine hydrochloride prepared by dissolving ranitidine in ethanol at 15° to 20° C, the ratio of ranitidine to ethanol being from about 1:2 to 1:4, adding aqueous hydrochloric acid to the solution thus obtained until a pH of 6± about 0.2 at about 30° C. is reached, and while maintaining this acidic pH and a temperature oil from about 30° to 35° C., adding seeding material of Form 1 ranitidine hydrochloride to the solution in a concentration of about 3% to 20% by weight, whereby crystallization of Form 1 ranitidine hydrochloride occurs.

15. The Form 1 ranitidine hydrochloride of claim 14, wherein the ratio of ranitidine to ethanol is about 1:3.6.

16. A process for preparing pure Form 1 ranitidine hydrochloride, which comprises: dissolving ranitidine in a solvent consisting essentially of methylene chloride; mixing the solution thus obtained with hydrochloric acid to form a reaction mixture; and crystallizing Form 1 ranitidine hydrochloride from the reaction mixture.

17. The process according to claim 16, further including the steps of heating the reaction mixture under reflux and while heating, stripping off water under azeotropic conditions.

18. The process according to claim 17, wherein the reaction mixture is heated under reflux for at least 4 hours.

19. The process according to claim 18, wherein the reaction mixture is heated under reflux for approximately 6.5 hours.

20. The process according to claim 16, wherein the ranitidine and hydrochloric acid are mixed with cooling at −5° to 10° C.

21. The process according to claim 16, wherein the ranitidine is dissolved in said solvent at room temperature.

22. The process according to claim 21, wherein the ratio of ranitidine to methylene chloride is from about 1:1 to 1:5.

23. The process according to claim 22, wherein the ratio of ranitidine to methylene chloride is about 1:4.

24. A process for preparing pure Form 1 ranitidine hydrochloride, which comprises: dissolving ranitidine in a solvent comprising methylene chloride; mixing the solution thus obtained with hydrochloric acid to form a reaction mixture; heating the reaction mixture under reflux and while heating, stripping off water under azeotropic conditions; and crystallizing Form 1 ranitidine hydrochloride from the reaction mixture.

25. The process according to claim 24, wherein the reaction mixture is heated under reflux for at least 4 hours.

26. The process according to claim 25, wherein the reaction mixture is heated under reflux for approximately 6.5 hours.

27. The process according to claim 24, wherein the ranitidine and hydrochloric acid are mixed with cooling at −50° to 10° C.

28. The process according to claim 24, wherein the ranitidine is dissolved in said solvent at room temperature.

29. The process according to claim 28, wherein the ratio of ranitidine to methylene chloride is from about 1:1 to 1:5.

30. The process according to claim 29, wherein the ratio of ranitidine to methylene chloride is about 1:4.

* * * * *